(12) United States Patent
Fanselow et al.

(10) Patent No.: US 10,983,079 B2
(45) Date of Patent: Apr. 20, 2021

(54) PROCESS AUTOMATION TECHNOLOGY SENSOR

(71) Applicant: Endress+Hauser Conducta GmbH+Co. KG, Gerlingen (DE)

(72) Inventors: Christian Fanselow, Geringswalde (DE); André Pfeifer, Schkopau (DE); Damian Mayerhofer, Dresden (DE); Thomas Nagel, Dresden (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 0 days.

(21) Appl. No.: 16/360,530

(22) Filed: Mar. 21, 2019

(65) Prior Publication Data

US 2019/0293580 A1   Sep. 26, 2019

(30) Foreign Application Priority Data

Mar. 26, 2018   (DE) .................... 10 2018 107 130.2

(51) Int. Cl.
| | |
|---|---|
| *G01N 25/18* | (2006.01) |
| *G01N 27/04* | (2006.01) |
| *G01N 27/02* | (2006.01) |
| *G01K 1/14* | (2021.01) |

(52) U.S. Cl.
CPC ............ *G01N 25/18* (2013.01); *G01K 1/14* (2013.01); *G01N 27/023* (2013.01); *G01N 27/04* (2013.01)

(58) Field of Classification Search
CPC ...... G01N 25/18; G01N 27/04; G01N 27/023; G01N 33/143; G01N 27/06; G01N 27/07; G01K 1/14; G01K 7/18; G01K 13/02; G01K 1/18

USPC ........................................................ 324/721
See application file for complete search history.

(56) References Cited

U.S. PATENT DOCUMENTS

| | | | | |
|---|---|---|---|---|
| 5,449,234 A | * | 9/1995 | Gipp ...................... | G01K 7/25 338/22 R |
| 2004/0261552 A1 | * | 12/2004 | Grundmann ........... | G01N 13/02 73/866.5 |
| 2006/0215731 A1 | * | 9/2006 | Gadonniex ............ | G01K 13/02 374/208 |
| 2007/0121701 A1 | * | 5/2007 | Gennissen .......... | G01L 19/0092 374/143 |

(Continued)

FOREIGN PATENT DOCUMENTS

| | | |
|---|---|---|
| CN | 105203230 A | 12/2015 |
| CN | 106199203 A | 12/2016 |

(Continued)

OTHER PUBLICATIONS

Translation of DE 102011085056 (Year: 2011).*

*Primary Examiner* — Christopher P McAndrew
(74) *Attorney, Agent, or Firm* — Christopher R. Powers; Endress+Hauser (USA) Holding Inc.

(57) ABSTRACT

The present disclosure includes a process automation technology sensor for detecting at least one measured variable of a medium, the sensor including a process connection for attaching the sensor to a container in which the medium is located; at least two webs which run essentially parallel to a longitudinal axis of the sensor, where the webs are arranged on the medium side extending from the process connection; and at least one first housing portion that comprises a temperature sensor, where the first housing portion is arranged between the webs.

19 Claims, 4 Drawing Sheets

(56) References Cited

U.S. PATENT DOCUMENTS

| | | | | |
|---|---|---|---|---|
| 2010/0040112 A1* | 2/2010 | Huck | ................ | G01K 1/08 |
| | | | | 374/183 |
| 2010/0321046 A1* | 12/2010 | Randall | ................ | G01N 27/07 |
| | | | | 324/696 |
| 2012/0216605 A1* | 8/2012 | Silveri | ................ | G01N 27/08 |
| | | | | 73/61.41 |
| 2013/0182745 A1* | 7/2013 | Hertel | ................ | G01R 3/00 |
| | | | | 183/185 |
| 2015/0168232 A1* | 6/2015 | Chu | ................ | B29C 45/14467 |
| | | | | 374/208 |
| 2015/0192478 A1* | 7/2015 | Rueth | ................ | G01K 1/14 |
| | | | | 374/143 |
| 2018/0038741 A1* | 2/2018 | Krishnamurthy | ........ | G01K 1/08 |

FOREIGN PATENT DOCUMENTS

| | | |
|---|---|---|
| CN | 107076570 A | 8/2017 |
| DE | 102009004530 A1 | 10/2009 |
| DE | 102011085056 A1 | 4/2013 |
| DE | 102013209060 A1 | 11/2014 |
| DE | 102014211771 A1 | 12/2015 |
| DE | 102015107087 A1 | 11/2016 |
| DE | 102015118123 A1 | 4/2017 |

* cited by examiner

PROCESS AUTOMATION TECHNOLOGY SENSOR

CROSS-REFERENCE TO RELATED APPLICATION

The present application is related to and claims the priority benefit of German Patent Application No. 10 2018 107 130.2, filed on Mar. 26, 2018, the entire contents of which are incorporated herein by reference.

TECHNICAL FIELD

The present disclosure relates to a process automation technology sensor for detecting at least one measured variable of a medium.

BACKGROUND

The technical problem the present disclosure is directed toward will be described briefly in reference to a conductivity sensor. However, the technical problem relates to many sensors that require a secondary measured variable, temperature, to determine the actual target value and for which a temperature sensor is used.

A simultaneous measurement of the temperature of the medium is necessary for detecting the conductivity of a material. In the case of existing sensors, the temperature sensor provided for detecting the same is integrated into the sensor within a housing. Applicant sells such conductivity sensors, for example, sold under the name "Indumax CLS54D", see for example https://www.de.endress.com/de/messgeraete-fuer-die-prozesstechnik/fluessigkeitsanalyse-produktuebersicht/leitfaehigkeit-induktiv-sensor-cls54d, last accessed Feb. 13, 2018.

The enclosure of the temperature sensor is often structurally designed such that it is arranged laterally along the sensor. As a result, the temperature sensor—to prevent mechanical damage—is designed to be short, and in its other dimensions relatively large. Thus, a thermal decoupling of the temperature sensor from the sensor cannot per se be realized to a sufficient degree, which negatively influences the response time of the temperature measurement.

SUMMARY

The object of the present disclosure is to improve the response time of the temperature measurement of sensors which require the temperature as a secondary measured variable.

The object is achieved by a sensor comprising: a process connection for attaching the sensor to a container in which a medium is located; at least two webs which run essentially parallel to a longitudinal axis of the sensor, wherein the webs are arranged on the medium side, extending from the process connection; and at least one first housing portion, including a temperature sensor, wherein the first housing portion is arranged between the webs.

Improving measuring performance can be realized as a result if the temperature sensor is introduced into an enclosure that is long relative to its other dimensions, that is to say, into the first housing portion, and is thus more thermally decoupled.

In contrast to the prior art, offsetting the temperature sensor toward the center of the sensor results in clearance around an enclosure, which is then delimited by the two webs. As a result, the temperature sensor is protected from mechanical damage. This makes it possible to lengthen the enclosure of the temperature sensor and to design it with a thinner wall thickness. This results in a faster response time of the temperature measurement due to thermal decoupling from the sensor housing.

In an embodiment, the first housing portion is arranged parallel to the webs. In an embodiment, the first housing portion is arranged on the process connection. In an embodiment, the sensor comprises exactly two webs and the webs are disposed opposite each other. In an embodiment, the first housing portion is arranged midway between the webs. In one embodiment, the first housing portion is arranged perpendicular to the webs.

In at least one embodiment, the sensor comprises one or more sensor elements for detecting the measured variable, and the webs connect the sensor element to the process connection. In an embodiment, the first housing portion, and thus the temperature sensor, are arranged on the one or more sensor elements. In an embodiment, the medium to be measured flows against or through at least one sensor element, and the temperature sensor is located behind a web relative to the flow direction of the medium. In another embodiment, the medium to be measured flows against or through at least one sensor element, and the temperature sensor is located beside the two webs relative to the flow direction of the medium.

In one embodiment, the temperature sensor is configured as a temperature sensor embedded in a circuit board. In such an embodiment, the temperature sensor is thus located on an intermediate layer of the printed circuit board. The printed circuit board is also used for contacting further elements, for instance the sensor elements, such as coils. The printed circuit board, along with other components of the sensor, is overmolded in the plastic without a temperature sensor subsequently having to be mounted. This achieves a fast response time due to the direct connection to the sensor housing, which is made of plastic, for example, which can be improved by overmolding the region around the temperature sensor with only thin walls.

This results in an assembly without manual or subsequent temperature sensor mounting. Complex wire fabrication and sources of faults can be eliminated. A rapid response time of the temperature sensor is also obtained by direct connection to the medium. No gaps result, and no heat conducting pastes are required.

In an embodiment, the sensor is designed as a conductivity sensor. In such an embodiment, the conductivity sensor comprises one or more sensor elements, in particular electrodes or coils, and the sensor elements are contacted via the printed circuit board.

A further aspect of the present disclosure is a method for the production of a sensor as described above, including at least the following step: overmolding the temperature sensor in an injection molding process such that the housing of the sensor is produced from one piece.

In an embodiment, the sensor element or the sensor elements are also overmolded. In an embodiment, the first housing portion is formed as a hollow extension between the webs, and the temperature sensor is inserted and/or pressed into this extension.

BRIEF DESCRIPTION OF THE DRAWING

The present disclosure is explained in more detail with reference to the following figures, in which.

In the figures, the same features are identified with the same reference symbols.

DETAILED DESCRIPTION

Figure 1:
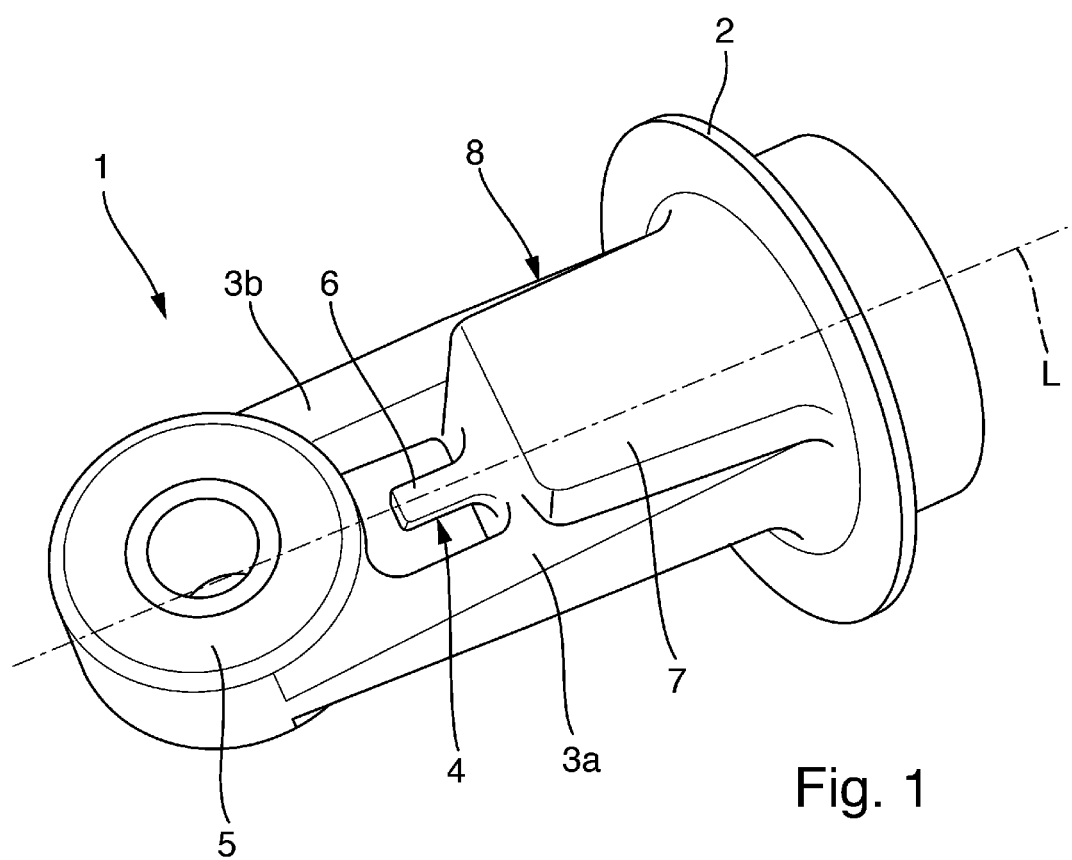
FIG. 1 shows an embodiment of a sensor of process automation technology according to the present disclosure.

The entirety of the claimed sensor is denoted by reference numeral 1 and is depicted in, amongst others, FIG. 1.

The inventive concept will be explained with reference to a conductivity sensor, in particular, an inductive conductivity sensor. However, the inventive concept may be applied to other types of sensors that require the temperature as secondary variable for detecting the primary variable. A wide range of sensors is conceivable from the field of process automation, such as conductive conductivity sensors, pH sensors, amperometric sensors, etc.

The sensor 1 includes a housing 8, as shown in FIG. 1. The housing 8 includes the entire enclosure of the sensor 1 including the first and second housing portions 6, 7 and including the sensor element 5 or the sensor elements, temperature sensor 4 and process connection 2.

In an embodiment, the second housing portion 7 includes electronics for processing measurement data.

Via the process connection 2, the sensor 1 is arranged on a process container (not shown) in which a medium to be measured is located. The sensor 1 includes one or more sensor elements 5, in the example two coils, for detecting the primary variable of the sensor 1. The coils themselves are not visible but are disposed in a housing portion designated by the reference numeral 5. For the sake of simplicity, the term "sensor elements 5" shall be used. The coils may be configured as toroidal coils, for example.

The sensor 1 includes a temperature sensor 4. The temperature sensor 4 may be arranged in the first housing portion 6. The first housing portion 6 is arranged between at least two webs, in the embodiment of FIG. 1, exactly between two webs 3a, 3b. The webs 3a, 3b are essentially parallel to a longitudinal axis L of the sensor 1. For the sake of clarity, the longitudinal axis L is only shown in FIG. 1.

Figure 4:
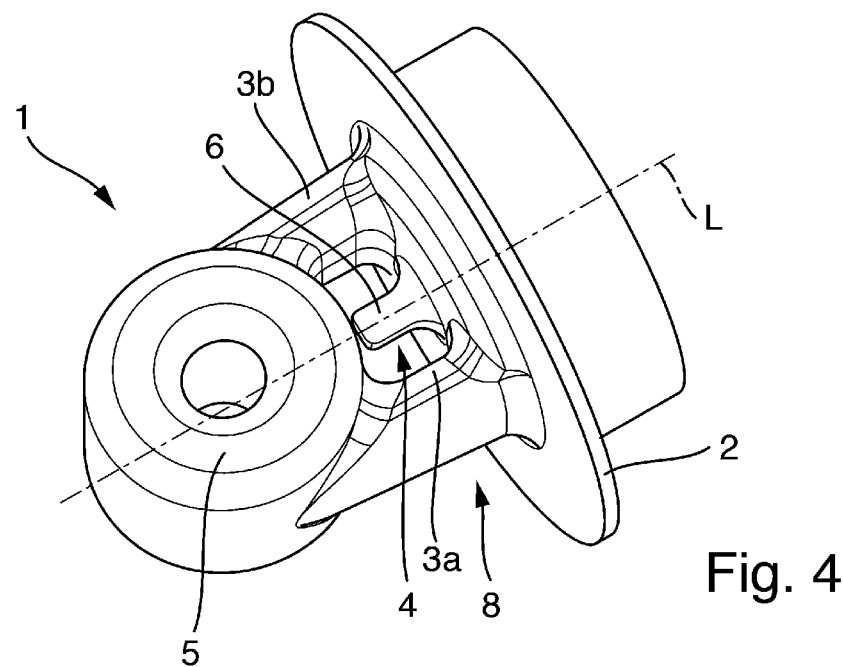
FIG. 4 shows a further embodiment of a sensor according to the present disclosure.

The first housing portion 6 is thus in a plane that is spanned by the axes of the webs 3a, 3b and is thus protected by the webs. The first housing portion 6 and thus the temperature sensor 4 are midway between the webs 3a, 3b. The first housing portion 6 is arranged parallel to the webs 3a, 3b. In FIGS. 1 and 4, the first housing portion 6 with the temperature sensor 4 is arranged at the process connection 2. In contrast to the prior art, displacement of the temperature sensor 4 toward the center of the sensor 1 results in clearance around an enclosure, that is to say the first housing portion 6, which is then delimited by the two webs 3a, 3b. This protects the temperature sensor 4 from mechanical damage. This further enables lengthening the enclosure, i.e., the first housing portion 6, of the temperature sensor 4, and designing the enclosure with a thinner wall thickness. This results in a faster response time of the temperature measurement due to thermal decoupling of the temperature sensor 4 from the sensor housing 8.

During the manufacture of the sensor enclosure 8, the enclosure of the temperature sensor 4, i.e., the first housing portion 6, is formed as a hollow projection between the webs 3a, 3b. The temperature sensor 4 is then introduced or pressed in from the direction of the process connection 2 of the later sensor.

Various designs of the temperature sensor 4 are possible, for instance, as a PTC resistor, NTC resistor, or platinum measuring resistor, such as a Pt100, Pt500, or Pt1000.

An embodiment of the enclosure of the temperature sensor 4 is realized by overmolding. In such an embodiment, the temperature sensor 4, for example on a carrier, is introduced into an injection molding tool, and then the housing 8 is produced by injection molding, thereby overmolding the temperature sensor 4. In some embodiments, the sensor elements 5 are also overmolded here. This embodiment makes it possible to attach the temperature sensor 4 to the sensor 1 from the direction of both the process connection 2 and the sensor element 5.

The temperature sensor 4 may have various configuration. Depending on the type and shape of the temperature sensor 4, the first housing portion 6 is correspondingly adapted and configured.

Figure 2:
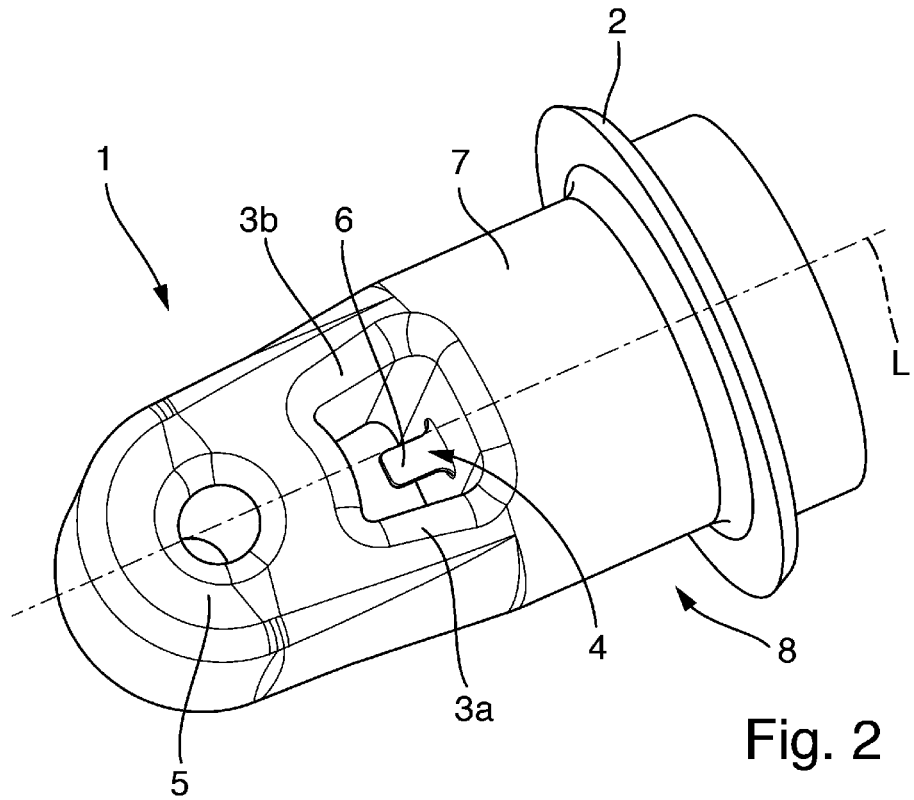
FIG. 2 shows another embodiment of a sensor according to the present disclosure.

In FIG. 2, the webs 3a, 3b have the same depth, e.g., into the sheet direction, as the sensor element 5. In addition, the second housing portion 7 is configured shorter compared to the embodiment of FIG. 1.

Figure 3:
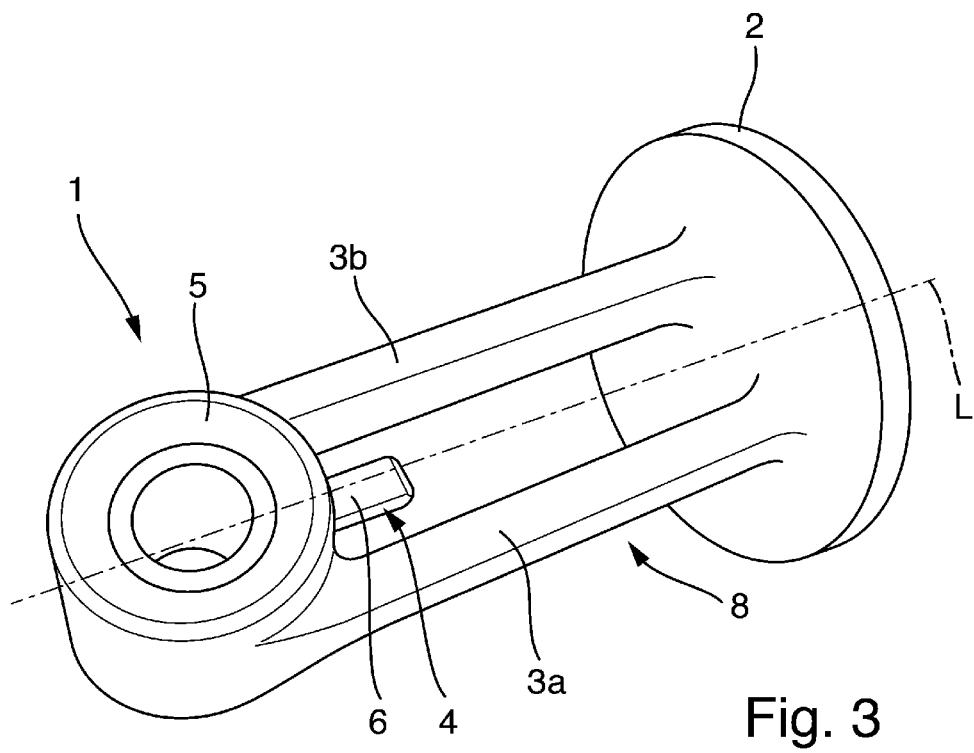
FIG. 3 shows a further embodiment of a sensor according to the present disclosure.

In FIG. 3, the first housing portion 6 is arranged with the temperature sensor 4 directly on the sensor element 5. FIG. 3 also shows a configuration with thinner webs 3a, 3b. FIG. 3 also shows a configuration without the second housing portion 7. Any necessary electronics are then arranged on the side away from the medium, i.e., the side of the process connection 2 that does not contact the media.

FIG. 4 shows a configuration which is again shorter compared to the embodiment of FIG. 2. The second housing portion 7 is also absent. The temperature sensor 4 is connected to the process connection 2 via the first housing portion 6.

Figure 5:
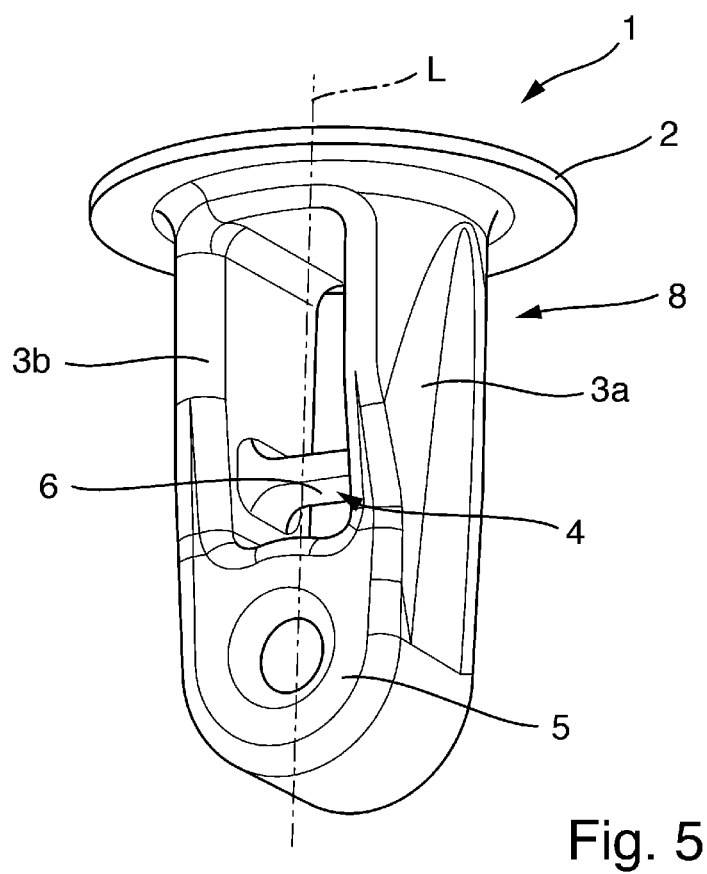
FIG. 5 shows a further embodiment of a sensor according to the present disclosure.

In FIG. 5, the temperature sensor 4 is arranged, not parallel to the webs 3a, 3b, *but perpendicular thereto.*

Figure 6:
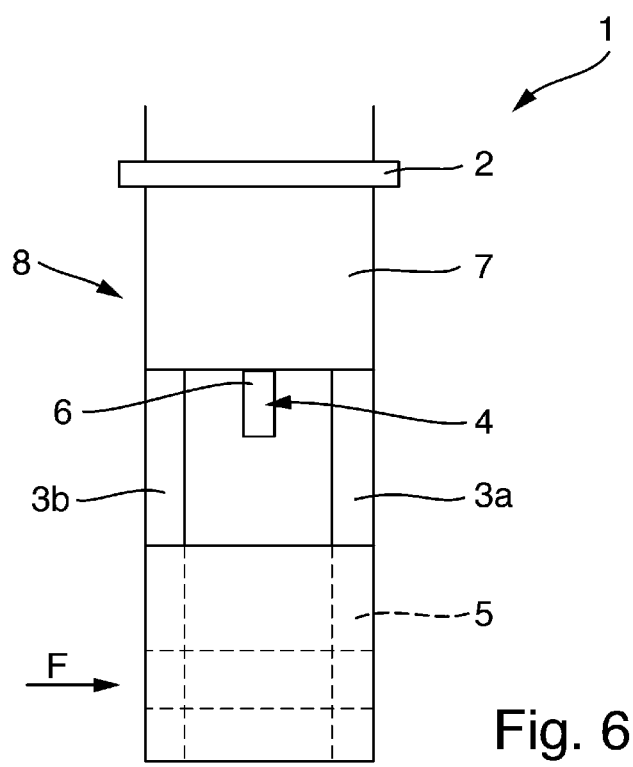
FIG. 6 shows a cross-sectional view of a further embodiment of a sensor according to the present disclosure.

FIG. 6 shows a cross-section of an embodiment. The medium to be measured flows through the sensor element 5 in the flow direction F of the medium. The first housing portion 6, together with temperature sensor 4, is located behind a web 3b relative to flow direction F of the medium. The temperature sensor 4 is thus better protected mechanically but might possibly be more unfavorably situated from a flow dynamics perspective, relative to the embodiments of the preceding figures.

Figure 7:
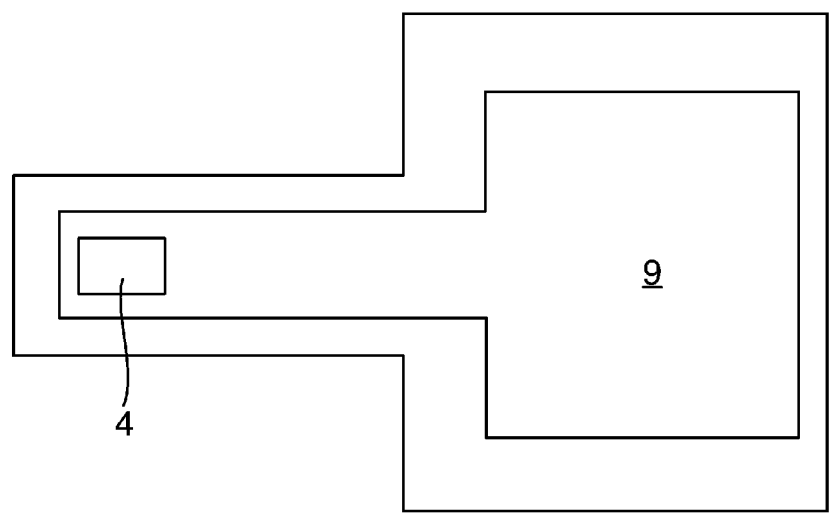
FIG. 7 shows an embodiment of a temperature sensor according to the present disclosure.

The temperature sensor 4 may be configured as an embedded temperature sensor. FIG. 7 shows a printed circuit board 9 in a plan view. The temperature sensor 4 may be located on an intermediate layer of the printed circuit board 9. The printed circuit board 9 is also used for contacting other elements, for example the sensor element 5, such as the coils. This printed circuit board 9 is overmolded in the plastic, together with other components of the sensor 1, without needing subsequent assembly of a temperature sensor 4. In such an embodiment, the direct connection to the sensor plastic achieves a fast response time, which can be improved by overmolding the region around the temperature sensor 4 with thin walls, for example, about 0.6-0.8 mm.

The invention claimed is:

1. A sensor of process automation technology for detecting at least one measured variable of a medium, the sensor comprising:
   a temperature sensor; and
   a housing, which encloses the temperature sensor from the medium, the housing including:
      a process connection adapted for attaching the sensor to a container in which the medium travels or is contained;
      at least two webs extending from the process connection and substantially parallel to a longitudinal axis of the sensor; and
      a first housing portion disposed between the webs, wherein the temperature sensor is disposed within the first housing portion,
   wherein the housing, including the process connection, the at least two webs and the first housing portion, are portions of a single integrated body.

2. The sensor of claim 1, wherein the first housing portion is arranged parallel to the at least two webs.

3. The sensor of claim 1, wherein the first housing portion extends from the process connection.

4. The sensor of claim 1, wherein the housing includes only two webs, which are arranged opposite each other about the longitudinal axis.

5. The sensor of claim 4, wherein the first housing portion is arranged midway between the webs.

6. The sensor of claim 1, wherein the first housing portion is arranged perpendicular to the webs.

7. The sensor of claim 1, further comprising one or more sensor elements configured to detect the measured variable and to enclose sensor components configured to detect the measured variable, wherein the webs connect the one or more sensor elements to the process connection.

8. The sensor of claim 7, wherein the first housing portion extends from at least one of the one or more sensor elements.

9. The sensor of claim 1, wherein the temperature sensor is embedded in a circuit board.

10. The sensor of claim 1, wherein the sensor is configured as a conductivity sensor.

11. The sensor of claim 10, wherein the sensor includes one or more electrodes or coils, each in electrical contact with the printed circuit board.

12. A method for manufacturing a sensor, the method comprising:
   providing a sensor configured to detect at least one measured variable of a medium, the sensor comprising:
      a temperature sensor; and
      a housing, which encloses the temperature sensor from the medium, the housing including:
         a process connection adapted for attaching the sensor to a container in which the medium travels or is contained;
         at least two webs extending from the process connection and substantially parallel to a longitudinal axis of the sensor; and
         a first housing portion disposed between the webs, wherein the temperature sensor is disposed within the first housing portion; and
   overmolding the temperature sensor using an injection molding process such that the housing of the sensor, including the process connection, the at least two webs and the first housing portion, is manufactured as a single integrated body.

13. The method of claim 12, wherein the first housing portion is arranged parallel to the at least two webs.

14. The method of claim 12, wherein the first housing portion extends from the process connection.

15. The method of claim 12, wherein the housing includes only two webs, which are arranged opposite each other about the longitudinal axis.

16. The method of claim 15, wherein the first housing portion is arranged midway between the webs.

17. The method of claim 12, wherein the temperature sensor is embedded in a circuit board.

18. The method of claim 17, wherein the sensor includes one or more electrodes or coils, each in electrical contact with the printed circuit board.

19. The method of claim 18, wherein the one or more electrodes or coils are overmolded with the temperature sensor.

* * * * *